United States Patent [19]
Kossmann et al.

[11] Patent Number: 6,066,782
[45] Date of Patent: May 23, 2000

[54] COMBINATION OF DNA SEQUENCES WHICH ENABLE THE FORMATION OF MODIFIED STARCH IN PLANT CELLS AND PLANTS, PROCESSES FOR THE PRODUCTION OF THESE PLANTS AND THE MODIFIED STARCH OBTAINABLE THEREFROM

[75] Inventors: Jens Kossmann, Berlin, Germany; Ivar Virgin, Stockholm, Sweden

[73] Assignee: Hoechst Schering AgrEvo GmbH, Berlin, Germany

[21] Appl. No.: 08/602,787

[22] PCT Filed: Sep. 8, 1994

[86] PCT No.: PCT/EP94/03031

§ 371 Date: Mar. 8, 1996

§ 102(e) Date: Mar. 8, 1996

[87] PCT Pub. No.: WO95/07355

PCT Pub. Date: Mar. 16, 1995

[30] Foreign Application Priority Data

Sep. 9, 1993 [DE] Germany .............................. 43 30 960

[51] Int. Cl.[7] ............................ C12N 15/29; C12N 15/84; C12N 15/82; C12P 19/04; A01H 5/00
[52] U.S. Cl. .......................... 800/284; 800/278; 800/286; 800/287; 800/294; 800/298; 800/317.2; 435/101; 435/193; 435/320.1; 435/419; 435/468; 435/469; 536/23.6; 536/24.5
[58] Field of Search ..................................... 435/69.1, 101, 435/193, 172.3, 320.1, 419, 468, 469; 536/23.6, 24.5, 24.1; 800/205, DIG. 42, 278, 284, 286, 287, 294, 298, 371.2

[56] References Cited

FOREIGN PATENT DOCUMENTS 9214827  3/1992  WIPO .
9211375  9/1992  WIPO .
9211382  9/1992  WIPO .

OTHER PUBLICATIONS

Journal Of Biological Chemistry, vol. 268, No.2, Jan. 15, 1993 Baltimore, MD US pp. 1391–1396 Takaha, T., et al. 'Disproportionating enzyme (4–alpha–glucanotransferase; EC 2.4.1.25) of potato. Purification, molecular clonging, and potential role in starch metabolism'.

Mol. Gen. Genet., vol.225, 1991 pp. 289–296 Visser, R.G.F., et al. 'Inhibition of the expression of the gene for granule–bound starch synthase in potato by antisense constructs'.

Kossmann et al. 1995. pp. 271–278 In: Carbohydrate Bioengineering, Peterson et al. (eds), Elsevier Science B.V.: Amsterdam.

Napoli et al. 1990. Plant Cell 2 : 279–289.

Smith et al. 1988. Nature 334: 724–726.

*Primary Examiner*—David T. Fox
*Attorney, Agent, or Firm*—Frommer Lawrence & Haug LLP

[57] ABSTRACT

A combination of DNA sequences is described which, in transgenic plant cells and plants, results in the formation of a modified starch which differs from starch synthesized naturally in the cells, especially in respect of its degree of branching and its phosphate content. A process for the production of genetically modified plants which are modified in respect of the physical and chemical properties of the synthesized starch due to the expression of artificially introduced DNA sequences, the plants obtainable by this process, and the modified starch obtainable from these plants, are also described.

15 Claims, 3 Drawing Sheets

Plasmid p35 S-anti-BE 13,6 kb

Plasmid p35 SH-anti-D 12,165 kb p35SH-anti-BE

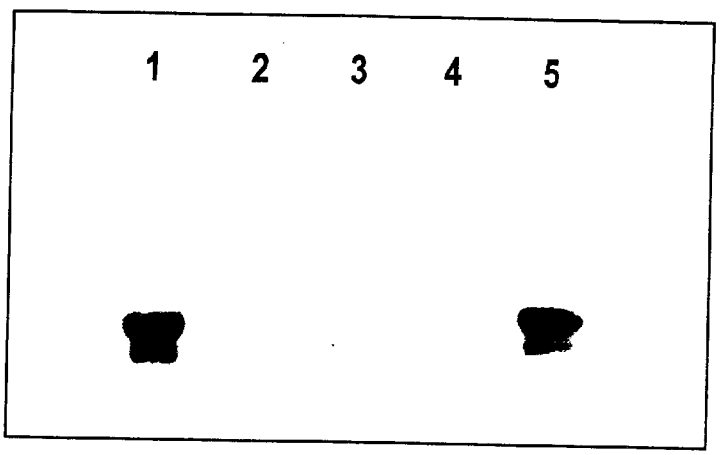
Fig. 6
Fig. 7
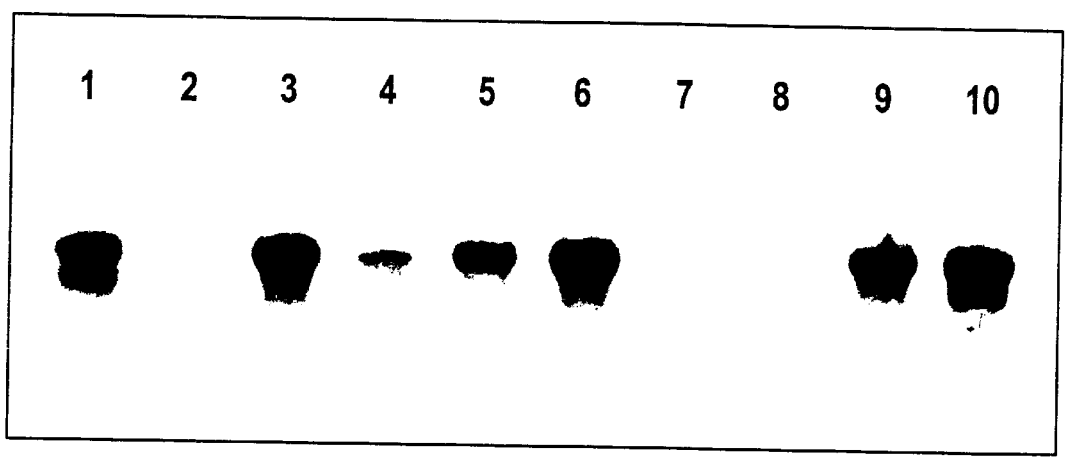
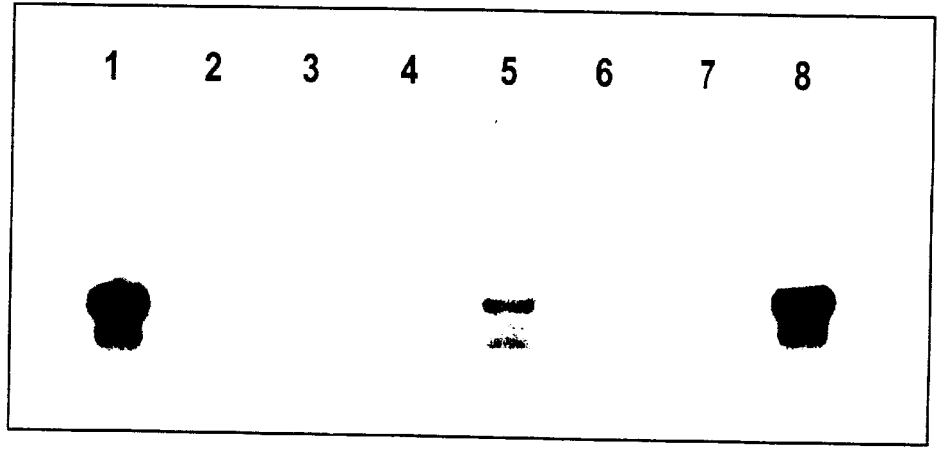
Fig. 8

COMBINATION OF DNA SEQUENCES WHICH ENABLE THE FORMATION OF MODIFIED STARCH IN PLANT CELLS AND PLANTS, PROCESSES FOR THE PRODUCTION OF THESE PLANTS AND THE MODIFIED STARCH OBTAINABLE THEREFROM

CROSS-REFERENCE TO RELATED APPLICATIONS

This application is a 371 of PCT/EP94/03031 filed Sep. 8, 1994.

The present invention relates to a combination of DNA sequences which, in transgenic plant cells and plants, results in a modification of the starch formed in the cells. The invention further relates to a process for the production of genetically modified plants which are modified in respect of the physical and chemical properties of the starch formed in comparison with the naturally formed starch due to the expression of artificially introduced DNA sequences, to the plant cells and plants obtainable by this process and to the modified starch obtainable from these plants.

BACKGROUND OF THE INVENTION

Together with oils, fats and proteins, polysaccharides such as starch are the essential renewable raw materials from plants.

A decisive obstacle to the use of renewable raw materials as industrial raw materials is the lack of materials whose form, structure or other physicochemical parameters precisely meet the requirements of the chemical industry. Two particular requirements of a raw material suitable for industrial use are that it is available in high purity and that it has a uniform chemical structure. The latter is important for ensuring that reactions proceed homogeneously during processing.

Although starch is a polymer made up of chemically uniform basic structural units, namely glucose molecules, it is a complex mixture of very varied molecular forms which differ in their degree of polymerization and the occurrence of branches in the glucose chains. The degree of branching determines inter alia the physicochemical properties of the starch in question and hence also its suitability for a very wide variety of applications. A distinction is made in particular between amylose starch, which is an essentially unbranched polymer made up of α-1,4-linked glucose molecules, and amylopectin starch, which in turn is a complex mixture of variously branched glucose chains. The branches arise from the occurrence of additional α-1,6 linkages.

In typical plants for starch production, such as maize or potato for example, the two forms of starch occur in proportions of about 25 parts of amylose to 75 parts of amylopectin.

To adapt the starch raw material to the different industrial applications, i.e. to vary its physicochemical properties, it is necessary inter alia to be able to influence the degree of branching of the starch.

With regard to the suitability of a basic material such as starch for its use in the industrial sector, it therefore seems desirable to provide processes for the production of amylogenic plants synthesizing a starch which is modified in comparison with the naturally occurring starch.

It is especially desirable to modify starch so that it has a modified degree of branching, e.g. a decrease or increase in the degree of branching, thereby forming a more uniform starch with a higher or lower amylose content.

An example of another property of interest for the industrial use of starch is the content of phosphate groups. Phosphate-containing starch has a broad application in a very wide variety of fields, e.g. in paper manufacture, in textile manufacture, as adhesives, in the food sector or in medicine. Furthermore, starch phosphate derivatives are suitable for use as emulsifiers. As the starch which occurs naturally in the majority of amylogenic plants contains only a very small proportion of phosphate groups, a specific exception here being starch formed in underground organs such as e.g. roots or potato tubers, phosphate groups have hitherto usually been introduced by means of chemical processes. To avoid the additional outlay on costs and time associated with such processes for the introduction of phosphate groups into starch, it seems desirable to provide processes which make it possible to modify plants so that they produce a starch which is modified in such a way as to have an increased content of phosphate groups.

As regards the degree of branching of starch, it is already known that for certain plant species, for example maize, varieties containing only amylopectin can be produced by mutagenesis, in which individual genes of the plant are inactivated. Likewise, for potatoes, a genotype which forms no amylose has been produced by the chemical mutagenesis of a haploid line (Hovenkamp-Hermelink et al., 1987, Theor. Appl. Genet. 75, 217–221). However, haploid lines, or the homozygous diploid or tetraploid lines developed therefrom, are unusable in agriculture. The mutagenesis technique is not applicable to the heterozygous tetraploid lines of agricultural interest since the inactivation of all the copies of a gene is technically impossible because of the presence of four different copies of the genotype.

Maize and pea varieties capable of producing amylose starch are also known, but the amylose concentration in the starch of these plants is only 60–80%. Furthermore, the mutagenesis process on which the production of these varieties is based cannot be applied to other plants, e.g. potatoes.

Visser et al. (1991, Mol. Gen. Genet. 225, 289) have moreover disclosed that potato varieties which form substantially pure amylopectin starch can be produced with the aid of genetic engineering methods, especially by antisense inhibition of the gene for the starch synthase bound to the starch granule.

WO 92/14827 has disclosed a branching enzyme of potato. This enzyme is designated as the Q enzyme (branching enzyme) of *Solanum tuberosum*. It is further known that with the aid of DNA sequences which contain the information for the branching enzyme of potato described in WO 92/14827, it is possible to produce transgenic plants in which the amylose/amylopectin ratio of the starch is modified, although the plants described in WO 92/14827 do not form a starch with a high amylose content.

The synthesis, degradation and modification of starch involves a large number of enzymes whose interaction has so far been only partially explained.

In the potato, the starch is synthesized primarily by the action of the starch synthase, which utilizes essentially ADP-glucose as the substrate for transferring a glucose residue onto the non-reducing end of a polyglucan. What other enzymes are involved in the synthesis of branched starch in the potato is largely unknown at the present time.

Again, several enzymes are involved in the modification and degradation of starch:

The starch phosphorylases, which utilize inorganic phosphate as a cosubstrate, degrade α-1,4 linkages up to four units before an α-1,6 branch and work from the non-reducing end. As an exoamylase, β-amylase has a high specificity for α-1,4 linkages. The least polymerized substrate is maltotetraose. Branching points bring an end to chain degradation, the last α-1,4 linkage before the branching point staying intact (Whelan, 1961, Nature 190, 954–957). The remaining polyglucans can be processed by transglycosylases, which possess both hydrolytic and synthesizing enzymic activity.

The Q enzyme (branching enzyme) and the T enzyme work as transglycosylases on the modification of the starch. The minimal substrate for the reaction catalyzed by the T enzyme is α-1,4-maltose, which is converted to the trisaccharide panose and glucose, forming an α-1,6 linkage (Whelan, 1961; Abdullah & Whelan, 1960, J. Biochem. 75, 12P). The Q enzyme catalyzes the same transglycosylation exclusively on glucans with a chain length of at least 40 units. Whereas the occurrence of several Q enzymes is known for other species such as maize (Singh & Preiss, 1985, Plant Physiol. 79, 34–40), only the branching enzyme described in WO 92/14827 has been detected in the case of *Solanum tuberosum*.

Another transglycosylase, the D enzyme, was first described in 1953 (in Nature 172, 158). Peat et al. (1956, J. Chem. Soc., Part XX, 44–55) describe it as a transglycosylase which transfers maltodextrin sub strates with two or more units, thereby producing exclusively α-1,4 linkages. The substrate must be made up of at least three units and there is a low specificity in respect of the acceptor. Takaha et al. (1993, J. Biol. Chem. 268, 1391–1396) describe the purification of the D enzyme of potato (EC 2.4.1.25) and the cloning of a cDNA. The purified enzyme accepts glucose as the recipient of the chain to be transferred, but the donor must be made up of at least three glucose units.

The authors do not describe what type of linkage is formed in the transglycosylation and assume that the D enzyme, or disproportionation enzyme, is probably involved not so much in the modification as in the degradation of the starch. It is not yet known whether other enzymes are involved in the modification of the starch. It is also not known what effects the modification of the activities of the T or D enzyme has on the structure of the starch formed in the cells, nor have said effects been studied to date. Since it has been supposed hitherto that the D enzyme is involved in the degradation of the starch, an inactivation or overexpression of the gene coding for the D enzyme would not be expected to have any effect on the basic structure of the starch formed.

Nothing is currently known about the enzymic reactions involved in the introduction of phosphate groups into starch. Enzymes responsible for the introduction of the phosphate groups have not been identified, nor is there a clear explanation as to which substrates act as phosphate group donors.

Therefore, no-one has yet succeeded in specifically modifying amylogenic plants by genetic engineering methods so that a starch can be produced therein which, in terms of its physicochemical properties, for example the amylose content or the degree of branching, is modified in such a way that it is more suitable for industrial processing than starch which occurs naturally in plants.

Furthermore, it is not yet known how an amylogenic plant can be specifically modified by means of genetic engineering methods so that the starch formed in these plants has a higher content of phosphate groups.

OBJECTS OF THE INVENTION

One object of the present invention is thus to provide a combination of DNA sequences with the aid of which amylogenic plants can be modified so as to produce a modified starch which, in comparison with starch which occurs naturally in plants, has various advantages with regard to industrial processing. Said advantages include for example an increased amylose content, a modified degree of branching, an increased content of phosphate groups, etc. Further objects of the invention are to provide transgenic plants or plant cells which synthesize a starch modified in this way, and to provide a process for the production of these plants.

SUMMARY OF THE INVENTION

It has now been found, surprisingly, that by introducing into plant cells a combination of known DNA sequences which code for a branching enzyme or a disproportionation enzyme of potato, it is possible to produce plants synthesizing a starch which is modified in comparison with naturally formed starch, this modified starch differing from naturally formed starch particularly in respect of the degree of branching and the phosphate content.

The present invention therefore provides a combination of DNA sequences consisting of a) the coding region of a branching enzyme or part thereof, and b) the coding region of a disproportionation enzyme or part thereof, which are fused to a promoter in the antisense orientation so that, after introduction into a plant genome in transgenic plants, their transcription produces transcripts which inhibit the synthesis of branching enzyme and disproportionation enzyme in the cells by means of an antisense effect, resulting in the synthesis, in the cells, of a modified starch which differs from starch synthesized naturally in the cells, especially in respect of its degree of branching and its phosphate content.

In particular, the degree of branching of the modified starch can be modified in such a way that reduced or increased branching occurs, so that a starch with a higher or lower proportion of amylose is synthesized. Alternatively, the two coding regions for the branching enzyme and the disproportionation enzyme can each be coupled to their own promoter in the antisense orientation and thus be transcribed independently of one another, or they can be fused to a common promoter.

BRIEF DESCRIPTION OF THE DRAWINGS

FIG. 6 shows a Northern blot analysis of total RNA from potato plants which have been produced by a two-stage process in which plant cells were first transformed with plascid p35S-anti-BE (DSM 9366) and, after selection and regeneration of transformants, plant cells of these transformants were transformed with plasmid p35SH-1-anti-D (DSM 9365).

FIG. 7 shows a Northern blot analysis of total RNA from potato plants which have been produced by a two-stage process in which plant cells were first transformed with plasmid p35S-anti-D (DSM 9365) and, after selection and regeneration of transformants, plant cells of these transformants were transformed with plasimid p35SH-anti-BE (DSM 9366).

FIG. 8 shows a Northern blot analysis of total RNA from potato plants which were produced by a one-stage process in which plant cells were transformed with plasmid p35S-anti-D-anti-BE (DSM 9367) and whole intact plants were regeneration from transformed cells.

DETAILED DESCRIPTION OF THE INVENTION

Figure 1:
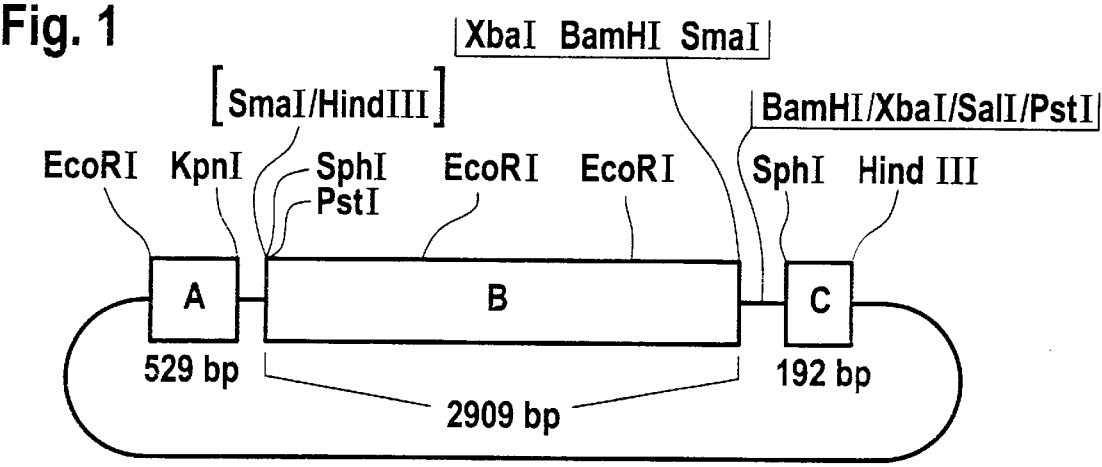
FIG. 1 shows plasmid p35S-anti-BE (DSM 6144) of 13.6 kb.

No-one has so far described a combination of DNA sequences which code for a branching enzyme with DNA sequences which code for a disproportionation enzyme, for the genetic modification of plant cells and plants in order to form, in the genetically modified plants, a starch which is modified in its physicochemical properties, especially in respect of the degree of branching and the phosphate content. The effect which the introduction of the novel combination of DNA sequences into a plant genome exerts on the physicochemical properties of the starch, especially the degree of branching and the content of phosphate groups, is surprising because there has been no indication hitherto of an involvement of the D enzyme either in the synthesis of starch and the introduction of branches, or in the introduction of phosphate groups into the starch formed. Indeed, according to the findings of Peat et al. (1956), the D enzyme is incapable of creating α-1,6 linkages.

The combination of DNA sequences preferably consists of the coding regions of the branching and disproportionation enzymes of *Solanum tuberosum*, the coding region of the branching enzyme being the sequence localized on recombinant plasmid p35SH-anti-BE (DSM 9366) or plasmid p35S-anti-BE (DSM 6144) and the coding region of the disproportionation enzyme being the sequence localized on recombinant plasmid p35SH-anti-D (DSM 8479) or plasmid p35S-anti-D (DSM 9365). It is possible to use either the whole coding regions or parts of these sequences, it being necessary for these parts to be long enough to have to an antisense effect in the cells. It is possible to use sequences down to a minimum length of 15 bp, preferably a length of 100 to 500 bp, or, for efficient antisense inhibition, especially sequences with a length of over 500 bp. As a rule, DNA molecules shorter than 5000 bp are used, preferably sequences shorter than 2500 bp.

When introduced simultaneously or successively into a plant genome in transgenic plants, the recombinant DNA sequences result in the formation of transcripts which modify the formation of enzymes of the starch metabolism so that, in the cells, a modified starch is synthesized which, in comparison with starch formed naturally in the cells, has inter alia an increased phosphate content and a modified degree of branching, especially a reduced but also an increased degree of branching, whereby the starch formed contains a higher or lower proportion of amylose.

Thus, for example, when introduced simultaneously or successively into a plant genome in transgenic plants, a combination of DNA sequences with the coding region of the branching enzyme on plasmid p35S-anti-BE (DSM 6144) and the coding region of the disproportionation enzyme on plasmid p35SH-anti-D (DSM 8479), or a combination of DNA sequences with the coding region of the branching enzyme on plasmid p35SH-anti-BE (DSM 9366) and the coding region of the disproportionation enzyme on plasmid p35S-anti-D (DSM 9365), results in the synthesis of transcripts which inhibit the synthesis of branching enzyme and disproportionation enzyme in the cells so that, in the cells, a modified starch is synthesized which differs from starch synthesized naturally in the cells, especially in respect of its degree of branching and its phosphate content.

Also, when introduced into a plant genome in transgenic plants, a combination of DNA sequences with the coding region of the branching enzyme and the coding region of the disproportionation enzyme on one plasmid, namely plasmid p35S-anti-D-anti-BE (DSM 9367), results in the synthesis of transcripts which inhibit the synthesis of branching enzyme and disproportionation enzyme in the cells so that, in the cells, a modified starch is synthesized which differs from starch synthesized naturally in the cells, especially in respect of its degree of branching and its phosphate content.

The present invention also provides processes for the production of transgenic plant cells and transgenic plants capable of synthesizing a modified starch which differs from starch synthesized naturally in the cells, especially in respect of its degree of branching and its phosphate content. Such transgenic plants can be produced by stably integrating one of the DNA combinations according to the invention into the genome of plant cells and regenerating whole plants from these transformed plant cells, the production being carried out by A) a one-stage process comprising the following steps:
  a) the preparation of a combination of DNA sequences from the following partial sequences:
    i) in each case one promoter which is active in plants and guarantees the formation of an RNA in the intended target tissue or the target cells,
    ii) in each case one coding region of a branching enzyme or part thereof and of a disproportionation enzyme or part thereof, fused to the promoter mentioned under i) in such a way as to form a transcript of the non-coding strand (antisense fusion), and
    iii) in each case one 3'-untranslated sequence which, in plant cells, results in the termination of transcription and the addition of poly-A residues onto the 3' end of the RNA, fused to the sequence mentioned under ii) in such a way that the 3'- untranslated sequence joins onto the 3' end of the non-coding strand mentioned under ii),
  b) the transfer and incorporation of the combinations of DNA sequences into a plant genome for the production of transgenic plant cells, and
  c) the regeneration of intact whole plants from the transformed plant cells, or B) a one-stage process comprising the following steps:
  a) the preparation of a combination of DNA sequences from the following partial sequences:
    i) a promoter which is active in plants and guarantees the formation of an RNA in the intended target tissue or the target cells,
    ii) a fusion of the coding region of a branching enzyme or part thereof and the coding region of a disproportionation enzyme or part thereof, fused together in such a way that both coding regions are read in the same direction (sense or antisense), and fused to the promoter mentioned under i) in such a way as to form a transcript of the non-coding strand of the fusion (antisense fusion), and
    iii) a 3'-untranslated sequence which, in plant cells, results in the termination of transcription and the addition of poly-A residues onto the 3' end of the RNA, fused to the sequence mentioned under ii) in such a way that the 3'-untranslated sequence joins onto the 3' end of the non-coding strand mentioned under ii), b) the transfer and incorporation of the combinations of DNA sequences into a plant genome for the production of transgenic plant cells, and c) the regeneration of intact whole plants from the transformed plant cells, or C) a two-stage process in which firstly a DNA sequence consisting of the following partial sequences:

iv) a promoter which is active in plants and guarantees the formation of an RNA in the intended target tissue or the target cells, v) a coding region of a branching enzyme or part thereof, fused to the promoter mentioned under iv) in such-a way as to form a transcript of the non-coding strand (antisense fusion), and vi) a 3'-untranslated sequence which, in plant cells, results in the termination of transcription and the addition of poly-A residues onto the 3' end of the RNA, fused to the sequence mentioned under v) in such a way that the 3'-untranslated sequence joins onto the 3' end of the non-coding strand mentioned under v), is transferred and incorporated into the genome of a plant cell, a whole plant is regenerated from the plant cell genetically modified in this way, and then, by repeat transformation in cells of this genetically modified plant, another DNA sequence, consisting of the following partial sequences:

vii) a promoter which is active in plants and guarantees the formation of an RNA in the intended target tissue or the target cells, viii) a coding region of a disproportionation enzyme or part thereof, fused to the promoter mentioned under vii) in such a way as to form a transcript of the non-coding strand (antisense fusion), and ix) a 3'-untranslated sequence which, in plant cells, results in the termination of transcription and the addition of poly-A residues onto the 3' end of the RNA, fused to the sequence mentioned under viii) in such a way that the 3'-untranslated sequence joins onto the 3' end of the non-coding strand mentioned under viii), is also transferred and incorporated into the genome of a plant cell, and finally the plant cells transformed in this way, containing both of said coding regions or parts thereof, are once again regenerated to form a whole plant, or D) a two-stage process as described under C), the coding region mentioned under v) coding not for a branching enzyme but for a disproportionation enzyme, and the coding region mentioned under viii) coding not for a disproportionation enzyme but for a branching enzyme.

The promoters used in the combination and mentioned under steps i), iv) and vii) of the process can be basically any promoters which are active in plants. For example, it is possible to use the 35S promoter of the cauliflower mosaic virus, which, in principle, causes a constitutive expression of downstream DNA sequences in all tissues of transformed plants. It is preferable to use promoters which are active in the starch-storing organs of the plants to be transformed. For maize and potato, these organs are the grains and tubers respectively. For the transformation of potato, it is possible in particular, but not exclusively, to use the tuber-specific B33 promoter of *Solanum tuberosum* or another promoter of a class I patatine gene. The coding regions of branching enzyme and disproportionation enzyme are fused to the promoter in such a way that the 3' end of the coding region is joined onto the 3' end of the promoter. This arrangement is designated as antisense orientation. The effect of the antisense orientation is that, in the expression of the transgene, the non-coding strand for the synthesis of a transcript is read. The non-coding transcript can neutralize the endogenous coding transcript in a genetically modified plant so that translation into a polypeptide does not take place. The enzymic activity of the branching and disproportionation enzymes is therefore irrelevant in the genetically modified plants. The success of the inhibition of translation depends inter alia on the amount of antisense transcripts active in the cell. To stabilize the transcripts formed by the combination of DNA sequences introduced, a termination and polyadenylation signal is therefore normally attached to the coding regions of branching enzyme and disproportionation enzyme. This can be for example the termination signal of the nopaline synthase gene from *Agrobacterium tumefaciens*.

The constructs formed by the fusion of the promoter, the coding region of the branching and disproportionation enzymes and the termination signal are preferably introduced into plant cells with the aid of suitable plasmids. The recombinant plasmids can contain the combination as a fusion of both of said coding DNA sequences, or parts of these sequences which are long enough to exert an antisense effect, or they can each contain an element of the combination. If the recombinant plasmids contain both of the DNA sequences indicated above, either the latter can be transcribed by a common promoter (process variant B)) or they can each be transcribed by their own promoter (process variant A)). If the recombinant plasmids contain both elements of the combination, transgenic plants containing the combination of DNA sequences according to the invention can be produced in a one-stage process. The plasmid used in the one-stage process according to the invention (process variant B)) is preferably plasmid p35S-anti-D-anti-BE (DSM 9367). If the recombinant plasmids each contain an element of the combination, they can be used successively for the transformation, so transgenic plants containing the combination of DNA sequences according to the invention can be produced in a two-stage process.

The recombinant plasmids used as a combination in the two-stage process according to the invention (process variants C) and D)) are preferably plasmids p35S-anti-BE (DSM 6144) and p35SH-anti-D (DSM 8479), or plasmids p35S-anti-D (DSM 9365) and p35SH-anti-BE (DSM 9366), or derivatives thereof. The plasmids are a further subject of the invention.

The invention also provides the plant cells and plants obtainable by the process according to the invention, which have integrated one or more of the DNA combinations according to the invention into the genome and are capable of synthesizing a modified starch which differs from the naturally formed starch, inter alia in respect of its degree of branching and its phosphate content.

In principle, the processes according to the invention can be applied to all plants. Plants of special interest are those which form starch as a storage substance, particularly productive plants. The processes according to the invention will preferably be applied to plants in which a branching enzyme and a disproportionation enzyme are involved in the modification of starch. This is preferably the potato, a productive plant.

The partial sequences from the novel combination of DNA sequences which code for the branching enzyme and the disproportionation enzyme of *Solanum tuberosum* can be replicated by cloning into plasmid vectors in bacteria. Examples of vectors are pBR322, pUC series, m13mp series, etc. The DNA sequences can be provided with linkers which allow a simple recloning into other plasmids. For the purpose of introduction into plants (see Example 6), it is possible preferably, but not exclusively, to use binary plasmids which contain a replication signal, for example for *Escherichia coli* and for *Agrobacterium tumefaciens*. If the binary plasmids contain T DNA elements, it is particularly easy to transfer the combination of DNA sequences into the genome of dicotyledonous plants. However, other methods are also available, for example transformation with the aid of ballistic processes, which is used for the transformation of monocotyledons (Potrykus, 1991, Ann. Rev. Plant Mol. Biol. Plant Physiol. 42, 205–225).

The transfer of the novel combination of DNA sequences, each of which contains a promoter, a coding region of the branching and disproportionation enzymes or a fusion of the two coding regions in the antisense orientation relative to the promoter, and a termination/polyadenylation signal, results in the formation, in the transgenic plants, of RNA molecules which, by interaction with the endogenous mRNAs of the branching enzyme and disproportionation enzyme, suppress their synthesis. This provides access to a starch which is modified in respect of its degree of branching and its phosphate content.

The modified starch formed in the transgenic plants can be isolated from the plants or from the plant cells by current methods and, after purification, processed for the production of foodstuffs and industrial products.

Deposits

Plasmid p35S-anti-BE (DSM 6144) and plasmid p35SH-anti-D (DSM 8479) were deposited on 20.08.1990 and 26.08.1993, respectively, in the Deutsche Sammiung von Mikroorganismen (DSM) in Brunswick, Federal Republic of Germany, under the terms of the Budapest Treaty.

The following additional plasmids were likewise deposited on 10.08.1994 in the Deutsche Sammiung von Mikroorganismen (DSM) in Brunswick under the terms of the Budapest Treaty:

| Plasmid p35S-anti-D | (DSM 9365) |
| Plasmid p35SH-anti-BE | (DSM 9366) |
| Plasmid p35S-anti-D-anti-BE | (DSM 9367) |

DETAILED DESCRIPTION OF THE FIGURES

FIG. 1 shows plasmid p35S-anti-BE (DSM 6144) of 13.6 kb. The plasmid contains the following fragments:

A=Fragment A (529 bp) comprises the 35S promoter of the cauliflower mosaic virus (CaMV), i.e. nucleotides 6909 to 7437 of CaMV B=Fragment B (2909 bp) comprises a DNA fragment with the coding region of the branching enzyme of *Solanum tuberosum*

C=Fragment C (192 bp) comprises the polyadenylation signal of the 3 gene of the T DNA of Ti plasmid pTiACH5, i.e. nucleotides 11749–11939

Figure 2:
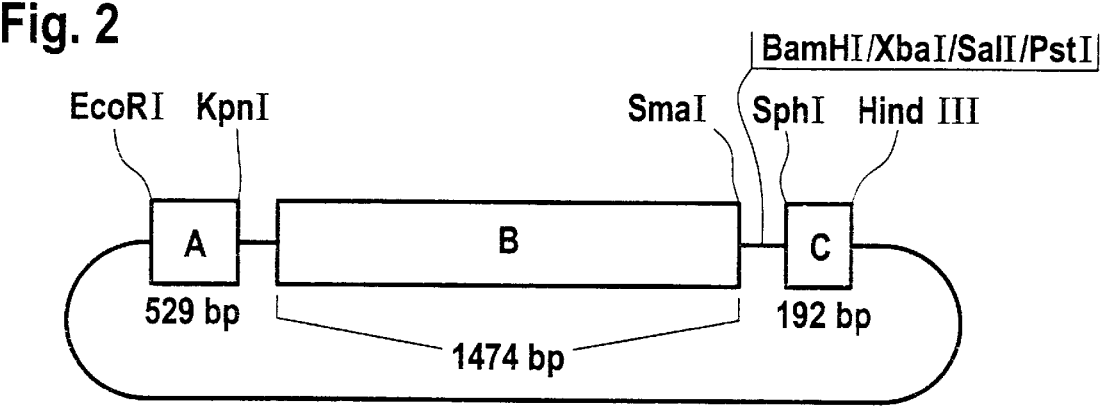
FIG. 2 shows plasmid p35SH-anti-D (DSM 8479) of 12.165 kb.

FIG. 2 shows plasmid p35SH-anti-D (DSM 8479) of 12.165 kb. The plasmid contains the following fragments:

A=Fragment A (529 bp) comprises the 35S promoter of the cauliflower mosaic virus (CaMV), i.e. nucleotides 6909 to 7437 of CaMV B=Fragment B (1474 bp) comprises a DNA fragment with the coding region of the disproportionation enzyme of *Solanum tuberosum*

C=Fragment C (192 bp) comprises the polyadenylation signal of the 3 gene of the T DNA of Ti plasmid pTiACH5, i.e. nucleotides 11749–11939

Figure 3:
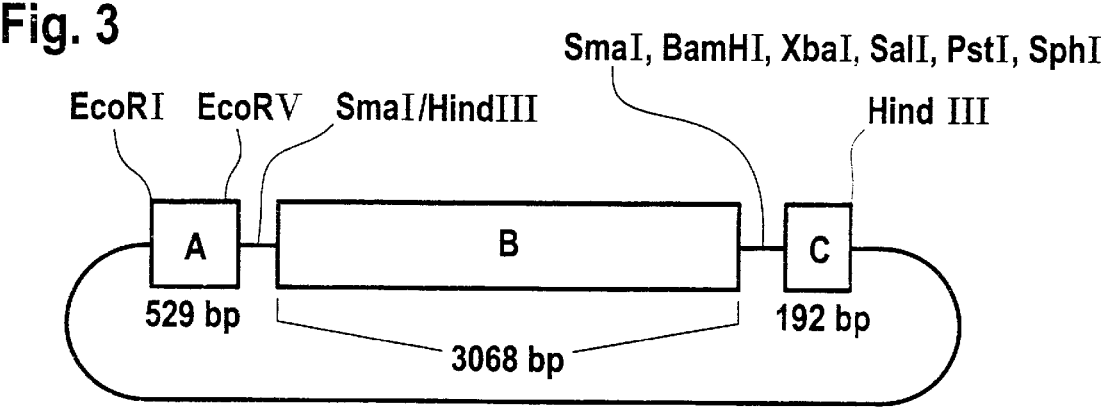
FIG. 3 shows plasmid p35SH-anti-BE (DSM 9366) of 13,75 kb.

FIG. 3 shows plasmid p35SH-anti-BE (DSM 9366). The plasmid is 13.75 kb long and contains the following DNA fragments:

A=Fragment A (529 bp) comprises the 35S promoter of the cauliflower mosaic virus (CaMV), i.e. nucleotides 6909 to 7437 of CaMV B=Fragment B (3068 bp) comprises a DNA fragment with the coding region of the branching enzyme of *Solanum tuberosum*

C=Fragment C (192 bp) comprises the polyadenylation signal of the 3 gene of the T DNA of Ti plasmid pTiACH5, i.e. nucleotides 11749–11939

Figure 4:
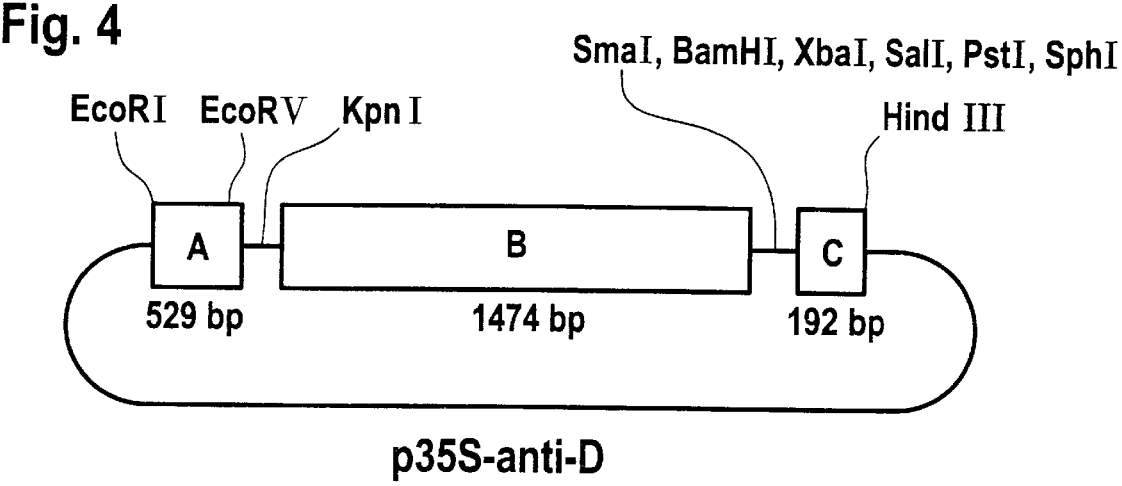
FIG. 4 shows plasmid p35S-anti-D (DSNM 9365) of 12.2 kb.

FIG. 4 shows plasmid p35S-anti-D (DSM 9365). The plasmid is 12.2 kb long and contains the following DNA fragments:

A=Fragment A (529 bp) comprises the 35S promoter of the cauliflower mosaic virus (CaMV), i.e. nucleotides 6909 to 7437 of CaMV B=Fragment B (1474 bp) comprises a DNA fragment with the coding region of the disproportionation enzyme of *Solanum tuberosum*

C=Fragment C (192 bp) comprises the polyadenylation signal of the 3 gene of the T DNA of Ti plasmid pTiACH5, i.e. nucleotides 11749–11939

Figure 5:
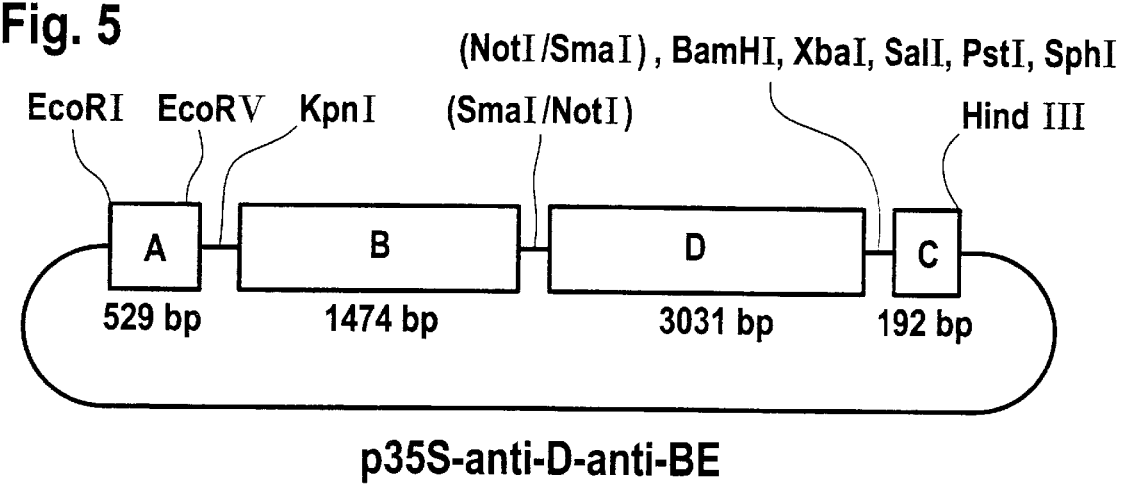
FIG. 5 shows plasmid p35S-anti-D)-anti-BE (DSM 9367) of 15.23 kb.

FIG. 5 shows plasmid p35S-anti-D-anti-BE (DSM 9367). The plasmid is 15.23 kb long and contains the following DNA fragments:

A=Fragment A (529 bp) comprises the 35S promoter of the cauliflower mosaic virus (CaMV), i.e. nucleotides 6909 to 7437 of CaMV B=Fragment B (1474 bp) comprises a DNA fragment with the coding region of the disproportionation enzyme of *Solanum tuberosum*

C =Fragment C (192 bp) comprises the polyadenylation signal of the 3 gene of the T DNA of Ti plasmid pTiACH5, i.e. nucleotides 11749–11939

D=Fragment D (3068 bp) comprises a DNA fragment with the coding region of the branching enzyme of *Solanum tuberosum*

FIG. 6 shows a Northern blot analysis of total RNA from potato plants which have been produced by a two-stage process in which plant cells were first transformed with plasmid p35S-anti-BE (DSM 9366) and, after selection and regeneration of transformands, plant cells of these transformands were transformed with plasmid p35SH-anti-D (DSM 9365).

The total RNA was tested for the presence of transcripts coding for branching enzyme or disproportionation enzyme. The cDNA molecules which code for these enzymes were used as hybridization probes for this purpose.

Bands 1 and 5: Wild-type potato plants (*Solanum tuberosum* c.v. *Desirée*)

Bands 2, 3 and 4: Three different transformed clones produced by the process described above, each of which contains a DNA combination according to the invention The upper of the two hybridization signals corresponds to transcripts coding for branching enzyme and the lower hybridization signal corresponds to transcripts coding for disproportionation enzyme.

FIG. 7 shows a Northern blot analysis of total RNA from potato plants which have been produced by a two-stage process in which plant cells were first transformed with plasmid p35S-anti-D (DSM 9365) and, after selection and regeneration of transformands, plant cells of these transformands were transformed with plasmid p35SH-anti-BE (DSM 9366).

The total RNA was tested for the presence of transcripts coding for branching enzyme or disproportionation enzyme. The cDNA molecules which code for these enzymes were used as hybridization probes for this purpose.

Bands 1 and 10: Wild-type potato plants (*Solanum tuberosum* c.v. *Desirée*)

Bands 2 to 9: Eight different transformed clones produced by the process described above, each of which contains a DNA combination according to the invention The upper of the two hybridization signals corresponds to transcripts coding for branching enzyme and the lower hybridization signal corresponds to transcripts coding for disproportionation enzyme.

FIG. 8 shows a Northern blot analysis of total RNA from potato plants which were produced by a one-stage process in which plant cells were transformed with plasmid p35S-anti-D-anti-BE (DSM 9367) and whole intact plants were regenerated from transformed cells.

The total RNA was tested for the presence of transcripts coding for branching enzyme or disproportionation enzyme. The cDNA molecules which code for these enzymes were used as hybridization probes for this purpose.

Bands 1 and 8: Wild-type potato plants (*Solanum tuberosum* c.v. *Desirée*)

Bands 2 to 7: Six different transformed clones produced by the process described above, each of which contains a DNA combination according to the invention The upper of the two hybridization signals corresponds to transcripts coding for branching enzyme and the lower hybridization signal corresponds to transcripts coding for disproportionation enzyme.

For a better understanding of the Examples on which this invention is based, the most important processes used are explained first.

EXAMPLE

1. Cloning Process

Vector pUC18 (Yanisch-Perron et al. (1985) Gene 33, 103–119) was used for the cloning.

For the plant transformation, the gene constructions were cloned into binary vector BIN19 (Bevan (1984) Nucl. Acids Res. 12, 8711–8720).

2. Bacterial Strains

*E. coi* strains BMH71-18 (Messing et al. (1977) Proc. Natl. Acad. Sci. USA 24, 6342–6346) or TB1 were used for the pUC vectors. TB1 is a recombination-negative tetracycline-resistant derivative of the strain JM101 (Yanisch-Perron et al. (1 985) Gene 33, 103–119). The genotype of the TB1 strain is as follows (Bart Barrel, private communication): F, traD36, proAB, lacI, lac ZdM15, d(lac, pro), SupE, thiS, recA, Sr1::Tn10(Tcr).

The plant transformation was carried out with the aid of *Agrobacterium tumefaciens* strain LBA4404 (Bevan (1984) Nucl. Acids Res. 12, 8711–8721), BIN19 derivative.

3. Transformation of *Agrobacterium tumefaciens*

In the case of BIN19 derivatives, the introduction of the DNA into the agrobacteria takes place by direct transformation using the method of Holsters et al. (1978, Mol. Gen. Genet. 163, 181–187). The plasmid DNA of transformed agrobacteria was isolated by the method of Birnboim et al. (1979, Nucl. Acids Res. 7, 1513–1523) and, after appropriate restriction cleavage, separated by gel electrophoresis.

4. Plant Transformation 10 small leaves of a sterile potato culture, wounded with a scalpel, were placed in 10 ml of MS medium with 2% of sucrose, which contained 30–50 μl of an *Agrobacterium tumefaciens* overnight culture grown under conditions of selection. After gentle shaking for 3–5 minutes, the Petri-dishes were incubated at 25° C. in the dark. After 2 days, the leaves were laid out on MS medium with 1.6% of glucose, 2 mg/l of zeatin-ribose, 0.02 mg/l of naphthylacetic acid, 0.02 mg/l of gib berellic acid, 500 mg/l of claforan, 50 mg/l of kanamycin and 0.8% of bacto-agar. After incubation for one week at 25° C. and 3000 lux, the concentration of claforan in the medium had been reduced by half. Further cultivation was carried out as described by Rocha-Sosa et al. (1989, EMBO Journal 8, 29).

5. Analysis of Genomic DNA From Transgenic Plants

Genomic plant DNA was isolated by the method of Rogers et al. (1985, Plant Mol. Biol. 5, 69–76). For the DNA analysis, 10–20 μg of DNA were subjected to appropriate restriction cleavage and then analyzed with the aid of Southern blots for integration of the DNA sequences to be studied.

6. Analysis of the Total RNA From Transgenic Plants

Total plant RNA was isolated by the method of Logemann et al. (1987, Analytical Biochem. 163, 16–20). For the analysis, in each case 50 μg of total RNA were tested with the aid of Northern blots for the presence of the desired transcripts.

7. Determination of the Phosphate Content of Starch Isolated From Transgenic Potato Plants To determine the phosphate content of the starch synthesized in transgenic plants, starch was isolated from potato tubers and 250 mg of this starch were suspended in 1 ml of 0.7 N HCl. The suspension was incubated for 4 h at 100° C. 800 ml of buffer (100 mM MOPS-KOH pH 7.5; 10 mM MgCl$_2$; 2 mM EDTA) were added to a 100 ml aliquot and the mixture was placed in a cuvette and neutralized by the addition of 100 ml of 0.7 N KOH. The following were added in succession: NAD (final con centration: 0.4 mM) and glucose 6-phosphate dehydrogenase from leuconostoc (Sigma) (final volume of the test batch: 1 ml). The change in absorption was measured at a wavelength of 340 nm.

The following Examples illustrate the subject of the invention without implying a limitation; they show firstly the construction of binary plasmids and then the production of transgenic potato plants containing the combination of DNA sequences.

An analogous procedure can also be used to transform other productive plants in which a branching enzyme and a disproportionation enzyme are involved in the modification of the starch.

Example 1

Construction of Binary Plasmid p35S-anti-BE

Plasmid p35S-anti-BE (DSM 6144) was prepared in accordance with the instructions given in WO 92/14827, the following steps being performed in particular:

In a cDNA library from tuber tissue of *Solanum tuberosum* var. *Desirée*, inserted into the expression vector λgtII, various clones were identified which were recognized by an antiserum directed against the branching enzyme (for the immunoassay procedure see Example 3, Western blot). These clones were used to isolate full-length clones from a cDNA library from growing tubers of *Solanum tuberosum*, inserted into the HindIII cleavage site of plasmid pUC1 9. A clone with an insertion of 2909 bp was used for further cloning.

To prepare plasmid p35S-anti-BE, the cDNA insertion was provided with the promoter of the 35S RNA of the cauliflower mosaic virus (CaMV) and with the polyadenylation signal of the octopine synthase of Ti plasmid pTiACH5, the orientation of the cDNA being chosen so that the non-coding strand is read starting from the promoter (antisense orientation). Plasmid p35S-anti-BE has a size of 13.6 kb and consists of the three fragments A, B and C, which are inserted into the polylinker of plasmid pBIN19 (Bevan, Nucl. Acids Res. 12, 8711–8721) (see FIG. 1).

Fragment A (529 bp) includes the 35S promoter of CaMV and comprises nucleotides 6909 to 7437 (Franck et al., Cell 21, 285–294). It was isolated as an EcoRI/KpnI fragment from plasmid pDH51 (Pietrzak et al., Nucl. Acid Res. 14, 5857–5868) and ligated between the EcoRI/KpnI cleavage sites of the polylinker of pBIN19 to give pBIN19-A.

Fragment C (192 bp) includes the polyadenylation signal of the 3 gene of the T DNA of Ti plasmid pTiACH5 (Gielen et al., EMBO J. 3, 835–846), i.e. nucleotides 11749–11939, which was isolated as a PvuII/HindIII fragment from plasmid pAGV40 (Herrera-Estrelia et al., Nature 303, 209–213) and, after the addition of SphI linkers onto the PvuII cleavage site, was ligated between the SphI and HindIII cleavage sites of pBIN19-A to give pBIN19-AC.

Fragment B contains the cDNA of 2909 bp of the bran ching enzyme of *Solanum tuberosum* and was isolated as a HindIII/SmaI fragment from the pUC19 derivative described above. After filling-in of the HindIII cleavage site with the aid of DNA polymerase, the fragment was ligated into the SmaI cleavage site of the derivative pBIN19-AC described above (see FIG. 1).

Example 2
Construction of Plasmid p35SH-anti-D

Using two synthetically prepared DNA oligonucleotides of the sequences:

5'-GCCCCCGGGCTTTTAAGTTCCTTG-3' and
5'-CAGGGTACCTAACATCTTAATCATC-3' as primers for a polymerase chain reaction on cDNA from tuber tissue of *Solanum tuberosum*, a copy of the coding region of the disproportionation enzyme was produced which, because of the specific sequence of the oligonucleotides, was provided with a KpnI cleavage site at the 3' end of the coding strand and with an SmaI cleavage site at its 5' end. These two cleavage sites make it possible to clone the coding region of the disproportionation enzyme in the antisense orientation between the KpnI and SmaI cleavage sites of binary plasmid pBIN19-HYG. Plasmid pBIN19-HYG carries the hphI gene for hygromycin resistance in the T DNA. Plants which have already been transformed with a pBIN19 derivative require the use of this plasmid in order to be able to undergo renewed transformation and selection. Plasmid p35SH-anti-D was prepared using a derivative of pBIN19-HYG which had been provided with fragments A and C described in Example 1 by the procedure described therein. This had produced plasmid pBIN19-HYG-AC.

Ligation of the product, cleaved with KpnI and SmaI, of the polymerase chain reaction for copying the coding region of the disproportionation enzyme, between the KpnI and SmaI cleavage sites of pBIN19-HYG-AC, gave plasmid p35SH-anti-D (see FIG. 2), which, like plasmid p35S-anti-BE described in Example 1, consists of three fragments, A, B and C, inserted into the polylinker of pBIN19-HYG-AC. Fragments A and C are identical to the corresponding fragments in Example 1 and fragment B comprises nucleotides 1777 to 303 of the disproportionation enzyme of *Solanum tuberosum* (Takaha et al., 1993).

Example 3
Construction of Binary Plasmid p35SH-anti-BE

Another clone, BE7, with an insertion of 3047 bp coding for the branching enzyme, was isolated, as described in Example 1, from a cDNA library from potato tuber tissue, inserted into the expression vector λZAPII (Kossmann et al., Mol. Gen. Genet. 230, 39–44).

As described in Examples 1 and 2, this cDNA molecule was inserted as fragment B into vector pBIN19-HYG-AC in the antisense orientation relative to the 35S promoter. The cDNA coding for the branching enzyme was isolated from the BE7 clone as an SmaI/HindIII fragment of 3068 bp. After filling-in of the HindIII-overlapping ends with the aid of the Klenow fragment of DNA polymerase I from *Escherichia coli*, the fragment was ligated into the SmaI cleavage site of the derivative pBIN19-HYG-AC described in Example 2. The resulting plasmid, p35SH-anti-BE, is illustrated in FIG. 3.

Example 4
Construction of Binary Plasmid p35S-anti-D

Analogously to Example 2, the PCR fragment described therein, coding for the disproportionation enzyme, was inserted as fragment B into vector pBIN19-AC described in Example 1, in the antisense orientation relative to the 35S promoter. The resulting plasmid, p35S-anti-D, is illustrated in FIG. 4.

Example 5
Construction of Binary Plasmid p35S-anti-D-anti-BE

The insertion described in Example 3, coding for the branching enzyme, was inserted as an NotI fragment (fragment D) of 3031 bp into plasmid p35S-anti-D described in Example 4, in the antisense orientation relative to the 35S promoter. After filling-in of the NotI-cleaved ends with the aid of the Klenow fragment of DNA polymerase I, the fragment was ligated into plasmid p35S-10 anti-D cleaved with SmaI. The resulting plasmid, p35S-anti-D-anti-BE, is illustrated in FIG. 5.

Example 6
Transformation of *Agrobacterium tumefaciens* with Binary Plasmids and Genetic Modification of Plants with the Aid of Transformed Agrobacteria To transform *Agrobacterium tumefaciens*, the binary plasmids from Examples 1 to 5 were introduced into the cells by direct transformation using the method of Höfgen & Willmitzer (1988, Nucl. Acids Res. 16, 9877). The plasmid DNA of transformed agrobacteria was isolated by the method of Birnboim et al. (1979, NucI. Acids Res. 7, 1513–1523) and, after appropriate restriction cleavage, analyzed by gel electrophoresis.

Agrobacteria in which the integrity of the binary plasmids described in Examples 1 to 5, after the transformation, had been identified by restriction analysis were used for the genetic modification of potato plants.

To transform e.g. potato plants, for example 10 small leaves of a sterile culture, wounded with a scalpel, are placed in 10 ml of MS medium with 2% of sucrose, which contains 30–50 µl of an *Agrobacterium tumefaciens* overnight culture grown under conditions of selection. After gentle shaking for 3–5 minutes, the Petri dishes are incubated at 25° C. in the dark. After 2 days, the leaves are laid out on MS medium with 1.6% of glucose, 2 mg/l of zeatin-ribose, 0.02 mg/l of naphthylacetic acid, 0.02 mg/l of gibberellic acid, 500 mg/l of claforan, 50 mg/l of kanamycin and 0.8% of bacto-agar. After incubation for one week at 25°C. and 3000 lux, the concentration of claforan in the medium has been reduced by half. Further cultivation was carried out as described by Rocha-Sosa et al. (1989, EMBO J. 8, 29).

The following three different procedures were chosen for introducing the combination of DNA sequences according to the invention into plants:

a) In one case, potato plants were transformed first with the plasmid described in Example 1 because the success of the antisense inhibition of the formation of the branching enzyme can easily be identified with the antiserum described in Example 1. Transgenic plants in which branching enzyme is no longer detectable are used for superinfection with plasmid p35SH-anti-D. For selection, hygromycin in a concentration of 3 mg/l is then used instead of kanamycin.

b) Analogously to the procedure described under a), potato plants were first transformed with the plasmid described in Example 3, in a reciprocal process, and an antiserum directed against the disproportionation enzyme was used to identify and select plants showing a greatly reduced expression of the disproportionation enzyme. These plants were then superinfected with the plasmid described in Example 4.

c) Alternatively, potato plants were transformed with plasmid p35S-anti-D-anti-BE, described in Example 5, and regenerants showing greatly reduced contents of both proteins were selected.

The success of the genetic modification of the plants can be tested by analyzing the total RNA for the absence of the mRNA of the Q and D enzymes. Total plant RNA is isolated by the method of Logemann et al. (1987, Anal. Biochem. 163, 16–20). For the analysis, in each case 50 µg of total RNA are examined with the aid of Northern blots for the absence of the Q and D enzyme transcripts. The results of such Northern blot analyses are shown in FIGS. 6, 7 and 8. It is clear that the overwhelming number of potato plants transformed by the various processes with the DNA combination according to the invention causes a substantial reduction in the transcripts coding for branching enzyme and disproportionation enzyme.

To test for the presence of the Q enzyme in transgenic plants, total protein was extracted from plant tissue and a Western blot analysis was then carried out with an appropriate antiserum. For this purpose, protein extracts are separated according to molecular weight by means of SDS-PAGE. After SDS-PAGE, protein gels are equilibrated for 15–30 minutes in transfer buffer for graphite electrodes (48 g/l of Tris, 39 g/l of glycine, 0.0375% of SDS, 20% of methanol) and then transferred at 4° C. onto a nitrocellulose filter at 1.3 mA/cm2 for 1–2 hours. The filter is saturated for 30 minutes with 3% of gelatin in TBS buffer (20 mM Tris/HCl pH 7.5; 500 mM NaCl). The filter is then incubated for 2 hours with the antiserum in a suitable dilution (1:1000–10,000 in TBS buffer) at room temperature, after which the filter is washed for 15 minutes each with TBS buffer, TTBS buffer (TBS buffer with 0.1% of sorbitan monolaurate 20 EO) and TBS buffer. After washing, the filter is incubated for 1 hour at room temperature with goat anti-rabbit (GAR) antibodies conjugated with alkaline phosphatase (1:7500 in TBS). The filter is then washed as described above is and equilibrated in AP buffer (100 mM Tris/HCl pH 9.5; 100 mM NaCl; 5 mM MgCl2). The alkaline phosphatase reaction is started by the substrate addition of 70 µl of 4-nitrotetra zolium (NBT) solution (50 mg/ml of NBT in 70% of dimethylformamide) and 35 µl of 5-bromo-4-chloro-3-indolyl phosphate (BCIP) (50 mg/ml of BCIP in dimethylformamide) in 50 ml of AP buffer. As a rule, the first signals can be observed after 5 minutes.

To determine the amylose/amylopectin content of the starch of transgenic potato plants which produce starch with a modified degree of branching, leaf fragments with a diameter of 10 mm are floated for 14 hours on 6% sucrose solution under continuous light. This light incubation induces greatly increased starch formation in the leaf fragments. After incubation, the amylose and amylopectin concentrations are determined by the method of Hovenkamp-Hermelink et al. (1988, Potato Research 31, 241–246).

The degree of branching (content of α-1,6 linkages), the chain length and the size of the starch granules are determined by the method of Morrison et al. (1990, Methods in Plant Biochemistry, Academic Press Imtd. 2, 323–352).

---

We claim:

1. A combination of isolated DNA molecules said combination comprising a first DNA molecule comprising a promoter and a DNA sequence encoding a branching enzyme derived from potato and a second DNA molecule comprising a promoter and a DNA sequence encoding a disproportionation enzyme derived from potato, the first and second DNA sequences in antisense orientation with respect to said promoters.

2. A method of producing a transgenic plant capable of synthesizing a modified starch, comprising the steps of:
   a) preparing a first isolated DNA molecule comprising a promoter which is active in plants and a DNA sequence encoding a branching enzyme derived from potato said DNA sequence in antisense orientation with respect to said promoter;
   b) preparing a second isolated DNA molecule comprising a promoter which is active in plants and a DNA sequence encoding a disproportionation enzyme derived from potato, said DNA sequence in antisense orientation with respect to said promoter;
   c) integrating the first and second isolated DNA molecules into the genome of a plant cell; and
   d) regenerating a whole plant from said transformed plant cell.

3. A method of producing a transgenic plant capable of synthesizing a modified starch, comprising the steps of:
   a) preparing an isolated DNA molecule comprising:
      i) a promoter which is active in plants;
      ii) a first region encoding a branching enzyme derived from potato;
      iii) a second region encoding a disproportionation enzyme derived from potato;
      wherein the first and second regions are in antisense orientation with respect to said promoter;
   b) integrating the isolated DNA Molecule into the genome of a plant cell; and
   c) regenerating a whole plant from said transformed plant cell.

4. A plant cell comprising:
   a) a first DNA region comprising, a promoter and a DNA sequence encoding a branching enzyme derived from potato; and
   b) a second DNA region comprising a promoter and a DNA sequence encoding a disproportionation enzyme derived from potato;
   wherein the first and second sequences are in antisense orientation with respect to said promoters; and
   wherein said plant cell is capable of synthesizing a modified starch relative to starch synthesized naturally in a plant with respect to degree of branching and phosphate content.

5. An isolated DNA molecule comprising a promoter, a first region encoding a branching enzyme derived from potato and a second region encoding a disproportionation enzyme derived from potato, whereby the first and second regions are in antisense orientation with respect to said promoter.

6. A plasmid comprising the isolated DNA molecule of claim 5.

7. A transformed plant cell comprising the isolated DNA molecule of claim 5.

8. A transformed plant comprising the plant cell of claim 7.

9. The plasmid of claim 6 which is p35S-anti-D-anti-BE (DSM 9367).

10. The combination of claim 1 wherein the first DNA molecule is plasmid p35S-anti-BE (DSM 6144) and the second DNA molecule is plasmid p35SH-anti-D (DSM 8479).

11. The combination of claim 1 wherein the first DNA molecule is plasmid p35SH-anti-BE (DSM 9366) and the second DNA molecule is plasmid p35S-anti-D (DSM 9365).

12. The method of claim 2 wherein the DNA sequence encoding a branching enzyme is localized on plasmid p35S-anti-BE (DSM 6144) and the DNA sequence encoding a disproportionation enzyme is localized on plasmid p35SH-anti-D (DSM 8479).

13. The method of claim 2 wherein the DNA sequence encoding a branching enzyme is localized on plasmid p35SH-anti-BE (DSM 9366) and the DNA sequence encoding a disproportionation enzyme is localized on plasmid p35S-anti-D (DSM 9365).

14. The method of claim 3 wherein the region encoding a branching enzyme and the region encoding a disproportionation enzyme are localized on plasmid p35S-anti-D-anti-BE (DSM 9367).

15. A transformed plant comprising the plant cell of claim 4.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: Solanum tuberosum
      (F) TISSUE TYPE: tuber tissue (xi) SEQUENCE DESCRIPTION: SEQ ID NO:1:

GCCCCCGGGC TTTTAAGTTC CTTG      24

```
(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Solanum tuberosum
        (F) TISSUE TYPE: tuber tissue (xi) SEQUENCE DESCRIPTION: SEQ ID NO:2:

CAGGGTACCT AACATCTTAA TCATC                                              25
```